US012599391B2

(12) United States Patent
Chen et al.

(10) Patent No.: US 12,599,391 B2
(45) Date of Patent: Apr. 14, 2026

(54) ELECTRODE BALLOON CATHETER AND HIGH-VOLTAGE GENERATION PROCESSING DEVICE

(71) Applicant: SHANGHAI MICROPORT ROTAPACE MEDTECH CO., LTD., Shanghai (CN)

(72) Inventors: Rende Chen, Shanghai (CN); Zhaohua Chang, Shanghai (CN); Bin Yue, Shanghai (CN); Xiaofei Ji, Shanghai (CN); Kai Li, Shanghai (CN); Tianxi Chi, Shanghai (CN); Yingzhong Yao, Shanghai (CN)

(73) Assignee: SHANGHAI MICROPORT ROTAPACE MEDTECH CO., LTD., Shanghai (CN)

( * ) Notice: Subject to any disclaimer, the term of this patent is extended or adjusted under 35 U.S.C. 154(b) by 278 days.

(21) Appl. No.: 18/552,147

(22) PCT Filed: Mar. 22, 2022

(86) PCT No.: PCT/CN2022/082191
§ 371 (c)(1),
(2) Date: Sep. 22, 2023

(87) PCT Pub. No.: WO2022/199568
PCT Pub. Date: Sep. 29, 2022

(65) Prior Publication Data
US 2024/0173044 A1 May 30, 2024

(30) Foreign Application Priority Data
Mar. 24, 2021 (CN) .......................... 202110315618.7

(51) Int. Cl.
*A61B 17/22* (2006.01)
*A61B 17/00* (2006.01)

(52) U.S. Cl.
CPC .. *A61B 17/22022* (2013.01); *A61B 17/00234* (2013.01); *A61B 2017/00292* (2013.01); *A61B 2017/22025* (2013.01)

(58) Field of Classification Search
CPC ........ A61B 17/00234; A61B 17/22022; A61B 18/1492; A61B 2017/00292;
(Continued)

(56) References Cited

U.S. PATENT DOCUMENTS 5,459,700 A 10/1995 Jacobs
9,993,292 B2 6/2018 Adams et al.
(Continued)

FOREIGN PATENT DOCUMENTS

CN 103566461 A 2/2014
CN 104619272 A 5/2015
(Continued)

*Primary Examiner* — Mohamed G Gabr
(74) *Attorney, Agent, or Firm* — MUNCY, GEISSLER, OLDS & LOWE, P.C.

(57) ABSTRACT

An electrode balloon catheter and a high-voltage generation processing device are provided. The electrode balloon catheter includes a balloon, an inner catheter and a shock wave generation component. The balloon is disposed over the inner catheter and radially expands or collapses as a result of filling an inflation fluid therein or evacuating the inflation fluid therefrom. The shock wave generation component includes a flexible circuit layer and an electrode arrangement. The flexible circuit layer is disposed on the inner catheter, and the electrode arrangement is provided on the inner catheter to be located within the balloon. The electrode arrangement is connected to the flexible circuit layer and connected to a high-voltage generation processing device via the flexible circuit layer. The flexible circuit layer enables the electrode balloon catheter to have a reduced passage size closer to the size of a pre-dilation balloon.

15 Claims, 7 Drawing Sheets

(58) Field of Classification Search
CPC ........... A61B 2017/00526; A61B 2017/22025;
A61B 2018/0022; A61B 2018/0041;
A61B 2018/00422; A61B 2018/00577;
A61B 2018/00642; A61B 2018/00708;
A61B 2018/00791; A61B 2090/064
See application file for complete search history.

(56) References Cited

U.S. PATENT DOCUMENTS

| | | | |
|---|---|---|---|
| 2012/0203255 A1 | 8/2012 | Hawkins et al. | |
| 2014/0005576 A1 | 1/2014 | Adams et al. | |
| 2018/0153568 A1* | 6/2018 | Kat-Kuoy | ........ A61B 17/22022 |

FOREIGN PATENT DOCUMENTS

| | | | |
|---|---|---|---|
| CN | 108452426 A | 8/2018 | |
| CN | 109303586 A | 2/2019 | |
| CN | 112472275 A | 3/2021 | |
| CN | 112914719 A | 6/2021 | |
| CN | 215651484 U | 1/2022 | |
| WO | WO 2016/109737 | 7/2016 | |

* cited by examiner

ELECTRODE BALLOON CATHETER AND HIGH-VOLTAGE GENERATION PROCESSING DEVICE

TECHNICAL FIELD

The present invention relates to the field of medical devices and, in particular, to an electrode balloon catheter and a high-voltage generation processing device.

BACKGROUND

Angioplasty is a surgical technique for mechanically restoring a stenotic vascular lumen to its native size. Conventional angioplasty procedures often utilize a balloon catheter to physically dilate a stenotic lesion and re-open the vessel. However, expansion of the balloon tends to tear or damage the adventitia of the vessel. Indirect breaking of calcified deposits or "stones" in the urinary and biliary tracts by the electrohydraulic effect can be utilized to destroy calcified deposits attached to the wall of a diseased blood vessel. That is, electrohydraulic lithotripsy can be applied in angioplasty. Electrohydraulic lithotripsy is a technique in which a liquid is rapidly vaporized in a strong electric field created by a high voltage into steam bubbles which expand outwards and, when bursting, will produce powerful shock waves that act on the surroundings of the liquid. In order to make use of the electrohydraulic effect in destroying calcified deposits, an electrode arrangement may be provided in a balloon and connected to an external pulse power supply by wires routed through a catheter. After the balloon is placed near a calcified region within a blood vessel, high-voltage pulses are applied to the electrode arrangement, generating shock waves which propagate through a conductive liquid contained in the balloon and strike a wall of the balloon and the calcified region. In this way, calcified deposits can be destroyed, and a stenotic blood vessel can be dilated, by the application of repeated pulses, without causing damage to the surrounding soft tissue, avoiding the problem of blood vessel wall damage possibly caused by balloon expansion associated with conventional angioplasty.

Existing electrode balloon catheters have the disadvantages as follows:

1) Their positive and negative electrode leads are wound on a catheter, leading to an increased outer diameter and degraded passage performance of the catheter. Consequently, when inserted into a human body, the electrode balloon catheters tend to encounter difficulties in passing through a stenotic segment of a blood vessel, and a hypotube at a proximal or distal joint may break after repeated attempts.

2) The electrodes of the electrode balloon catheter are arranged in multiple layers, likewise leading to an increased catheter outer diameter, degraded catheter performance in passing through a blood vessel and possible breakage of a hypotube.

3) Balloon burst may occur during the delivery of shock waves, and if there is not a suitable hydraulic pressure feedback system in the catheter, this may lead to direct application of high-voltage pulses to the human body, which may cause a safety accident.

4) During treatment with these electrode balloon catheters, the balloon will remain in an expanded configuration for a long period of time, with its outer surface completely fitting on the blood vessel wall, thus occluding the blood vessel. As a consequence, a short-time ventricular capture or shock may happen.

Therefore, for electrode balloon catheter manufacturers, in order to solve the problem of difficult passage or even possible component breakage during intervention associated with conventional electrode balloon catheters, there is an urgent need for developing a novel electrode balloon catheter with a reduced passage size closer to the size of a pre-dilation balloon.

SUMMARY OF THE INVENTION

It is an object of the present invention to provide an electrode balloon catheter and a high-voltage generation processing device. The electrode balloon catheter has a smaller passage size closer to the size of a pre-dilation balloon, thereby solving the problem of difficult passage or even possible component breakage during intervention associated with conventional electrode balloon catheters.

To this end, the present invention provides an electrode balloon catheter comprising a balloon, an inner catheter and a shock wave generation component, the balloon disposed over the inner catheter and configured to radially expand or collapse as a result of filling an inflation fluid therein or evacuating the inflation fluid therefrom, the shock wave generation component comprising a flexible circuit layer and an electrode arrangement, the flexible circuit layer disposed on the inner catheter, the electrode arrangement provided on the inner catheter so as to be located within the balloon, the electrode arrangement connected to the flexible circuit layer and configured to be connected to a high-voltage generation processing device via the flexible circuit layer.

Optionally, the flexible circuit layer may have a thickness not exceeding 0.2 mm in a radial direction of the inner catheter.

Optionally, the flexible circuit layer may be provided on the inner catheter by adhesive bonding, printing, electroplating, 3D printing or vapor deposition.

Optionally, the electrode balloon catheter may further comprise a pressure sensor, which is disposed at a distal end of the inner catheter and configured to monitor resistance on the electrode balloon catheter and provide a resistance signal.

Optionally, the pressure sensor may be ring-shaped and disposed over the distal end of the inner catheter.

Optionally, the electrode balloon catheter may further comprise a hydraulic pressure sensor, which is disposed on the inner catheter and configured to monitor in real time an internal inflation pressure of the balloon and provide an inflation pressure signal.

Optionally, the electrode balloon catheter may further comprise an outer catheter disposed over the inner catheter so as to communicate with the balloon, wherein the hydraulic pressure sensor is provided on an outer surface of the inner catheter or an inner surface of the outer catheter.

Optionally, the electrode balloon catheter may further comprise a temperature sensor, which is disposed on an outer surface of the inner catheter or an inner surface of the outer catheter and configured to monitor an internal temperature of the balloon in real time and provide a temperature signal.

To the above end, the present invention also provides a high-voltage generation processing device configured for communicative connection with the electrode balloon catheter as defined above. The high-voltage generation processing device comprises a logic processing unit and a high-voltage generation unit, the logic processing unit electrically and communicatively connected to the high-voltage generation unit and configured to turn on and off the high-voltage generation unit, the logic processing unit electrically and communicatively connected to the hydraulic pressure sensor in the electrode balloon catheter and configured to receive an inflation pressure signal from the hydraulic pressure sensor and, when an inflation pressure drop rate or an absolute value of an inflation pressure difference indicated in the inflation pressure signal received by the logic processing unit exceeds a preset threshold, cut off the electrical and communicative connection with the high-voltage generation unit.

Optionally, the high-voltage generation processing device may further comprise a display unit connected to the logic processing unit, wherein when an inflation pressure indicated in the inflation pressure signal exceeds a preset operating pressure, the logic processing unit passes the inflation pressure signal on to the display unit which then provides a prompt signal upon receiving the inflation pressure signal.

Optionally, the logic processing unit may be further configured to receive a resistance signal from the pressure sensor in the electrode balloon catheter, and when resistance indicated in the resistance signal exceeds a preset threshold, pass the resistance signal on to the display unit which then provides an alarm signal upon receiving the resistance signal.

Optionally, the logic processing unit may be further configured to receive a temperature signal from the temperature sensor in the electrode balloon catheter, and when a temperature indicated in the temperature signal exceeds a preset threshold, cut off the high-voltage generation unit.

Optionally, the high-voltage generation processing device may further comprise an amplifying circuit, one end of the amplifying circuit connected to the logic processing unit, a further end of the amplifying circuit connected to the hydraulic pressure sensor, a touch sensor or a temperature sensor in the electrode balloon catheter.

Optionally, the high-voltage generation processing device may further comprise a timer, which is connected to the logic processing unit and configured to be started when an inflation pressure indicated in the inflation pressure signal received by the logic processing unit reaches a preset inflation pressure and send a timeout signal to the logic processing unit after a predetermined period of time elapses, wherein upon receiving the timeout signal, the logic processing unit passes the timeout signal on to the display unit, which then provides a prompt signal upon receiving the timeout signal.

Optionally, the high-voltage generation processing device may further comprise a sampling circuit for detecting a voltage signal of the high-voltage generation unit and the presence of a short circuit in the electrode arrangement or the flexible circuit layer in the electrode balloon catheter.

The present invention provides an electrode balloon catheter and a high-voltage generation processing device. The electrode balloon catheter includes a balloon, an inner catheter and a shock wave generation component. The balloon is disposed over the inner catheter and radially expands or collapses under the action of filling and evacuation of an inflation fluid therein and therefrom. The shock wave generation component includes a flexible circuit layer and an electrode arrangement. The flexible circuit layer is disposed on the inner catheter, and the electrode arrangement is provided on the inner catheter so as to be located within the balloon. The electrode arrangement is connected to the flexible circuit layer and configured to be connected to a high-voltage generation processing device via the flexible circuit layer. With this arrangement, the flexible circuit layer enables the electrode balloon catheter to have a reduced passage size closer to the size of a pre-dilation balloon, which imparts to the electrode balloon catheter improved performance in passage within a human body during intervention without breakage of any component therein.

BRIEF DESCRIPTION OF THE DRAWINGS

Those of ordinary skill in the art would appreciate that the accompanying drawings are provided to facilitate a better understanding of the present invention and do not limit the scope thereof in any sense, in which.

Figure 1:
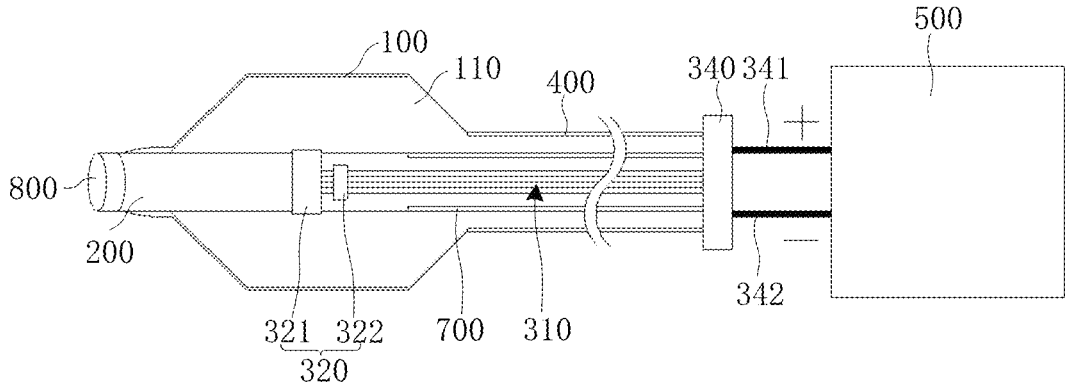
FIG. 1 is a schematic illustration of an electrode balloon catheter according to a first embodiment of the present invention.

In these figures, 100 denotes a balloon; 110, an inflation fluid;

200, an inner catheter;

310, a flexible circuit layer; 311, a positive electrode lead; 312, a negative electrode lead; 320, an electrode arrangement; 3201, a first electrode; 3202, a second electrode; 3203, an accommodation structure; 3204, an insulating connecting member; 3205, pointed protrusions; A, a first connecting feature; B, a second connecting feature; C, a third connecting feature; D, a fourth connecting feature; E, electrode leads; 321, a positive electrode; 322, a negative electrode; 340, a catheter connecting member; 341, an external positive electrode lead; 342, an external negative electrode lead;

400, an outer catheter;

500, a high-voltage generation processing device; 510, a logic processing unit; 511, a logic processor; 520, a high-voltage generation unit; 521, a high-voltage generator; 522, a high-voltage resistor; 523, a high-voltage capacitor; 530, an amplifying circuit; 540, a display unit; 541, a monitor; 550, a trigger element; 550a, a trigger device; 551, a first switch; 552, a second switch; 560, a sampling circuit; 570, a connector; 580, an operating handle;
600, a temperature sensor;
700, a hydraulic pressure sensor; and
800, a pressure sensor.

DETAILED DESCRIPTION

Objects, advantages and features of the present invention will become more apparent upon reading the following more detailed description of the present invention with reference to the accompanying drawings. Note that the figures are provided in a very simplified form not necessarily drawn to exact scale and for the only purpose of facilitating easy and clear description of the embodiments. In addition, structures shown in the figures are usually part of actual structures. In particular, as the figures tend to have distinct emphases, they are often drawn to different scales.

As used herein, the singular forms "a", "an" and "the" include plural referents, unless the context clearly dictates otherwise. As used herein, the term "or" is generally employed in the sense of "and/or", unless the context clearly dictates otherwise. In the following, for ease of description, the terms "distal end" and "proximal end" may be used. The term "distal end" refers to an end closer to a patient and farther away from an operator, and the term "proximal end" refers to an end farther away from the patient and closer to the operator. Additionally, the following description sets forth numerous specific details in order to provide a more thorough understanding of the present invention. However, it will be apparent to those skilled in the art that the present invention can be practiced without one or more of these specific details. In other instances, well-known technical features have not been described in order to avoid unnecessary obscuring of the invention.

In embodiments of the present invention, there are provided an electrode balloon catheter and a high-voltage generation processing device. The electrode balloon catheter includes a balloon, an inner catheter and a shock wave generation component. The balloon is disposed over the inner catheter and can radially expand or collapse under the action of filling or evacuation of an inflation fluid. The shock wave generation component includes a flexible circuit layer and an electrode arrangement. The flexible circuit layer is disposed on the inner catheter, and the electrode arrangement is provided on the inner catheter within the balloon. The electrode arrangement is connected to the flexible circuit layer and thereby to the high-voltage generation processing device via the flexible circuit layer. With this arrangement, the flexible circuit layer can improve performance of the electrode balloon catheter in passage in a human body during intervention while avoiding breakage of any component in the electrode balloon catheter by enabling the electrode balloon catheter to have a smaller passage size closer to the size of a pre-dilation balloon. The high-voltage generation processing device is configured to establish a signal connection with the electrode balloon catheter as defined above and includes a logic processing unit and a high-voltage generation unit. The logic processing unit is configured to receive an inflation pressure signal from a hydraulic pressure sensor in the electrode balloon catheter. When an inflation pressure drop rate or an absolute value of an inflation pressure difference indicated in the inflation pressure signal received by the logic processing unit exceeds a preset threshold, the logic processing unit will turn off the high-voltage generation unit, thereby ensuring stability of the inflation pressure within the balloon in real time and avoiding potential hazards and safety accidents. The high-voltage generation processing device further includes a mechanism, which implements timer logic to avoid the balloon from fitting at its outer surface against the wall of a blood vessel and thereby occluding the blood vessel for a period of time that is sufficiently long to cause a ventricular capture or shock.

The present invention will be further described below with reference to the accompanying drawings.

Embodiment 1

Figure 2:
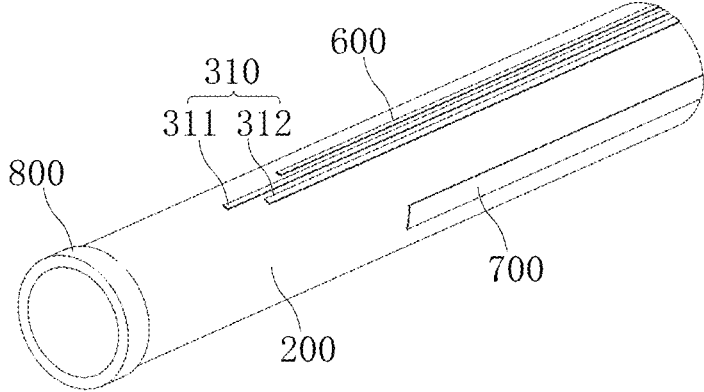
FIG. 2 is a schematic illustration of an inner catheter according to the first embodiment of the present invention.
Figure 3:
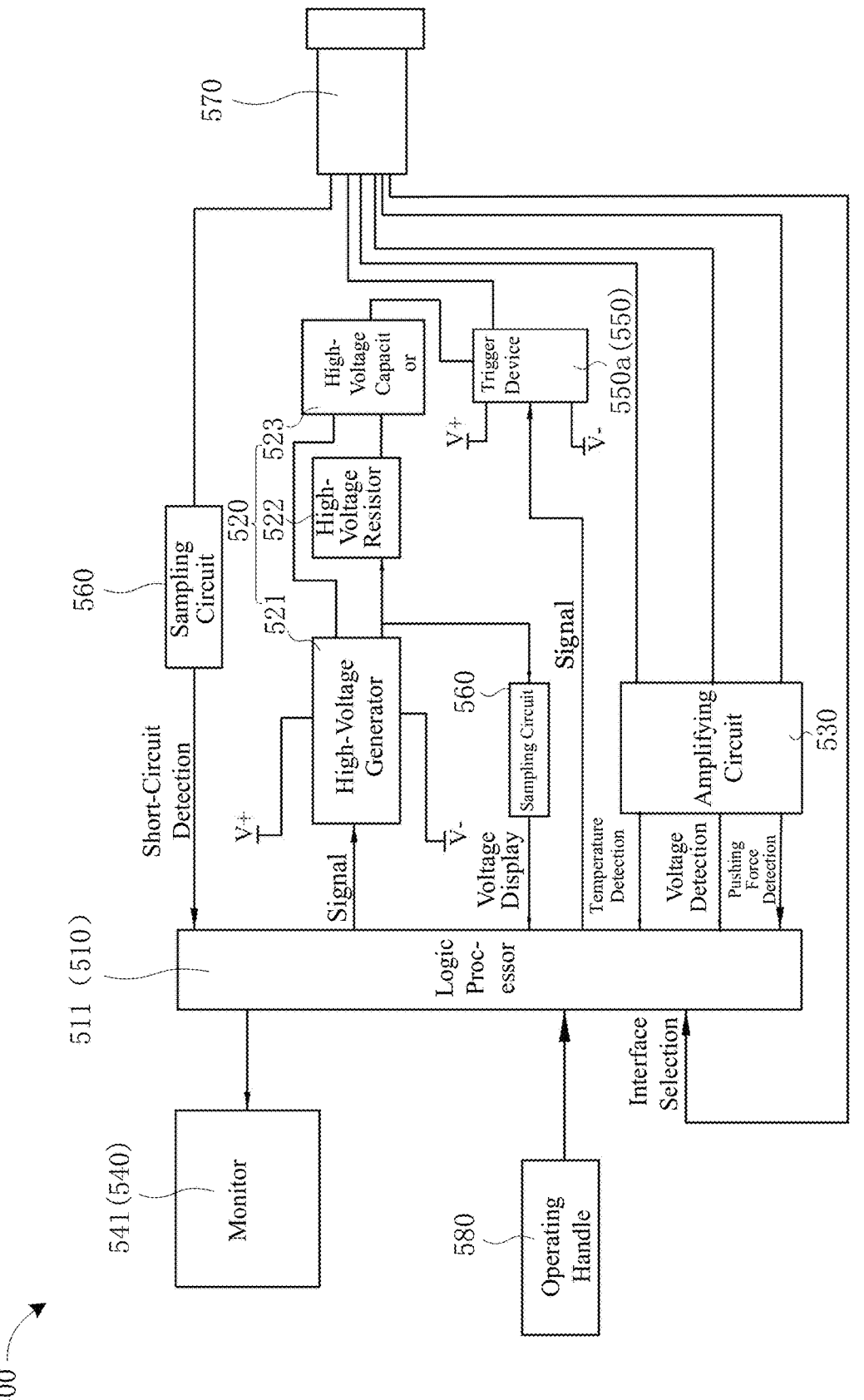
FIG. 3 is a circuit diagram of a high-voltage generation processing device according to the first embodiment of the present invention.
Figure 4:
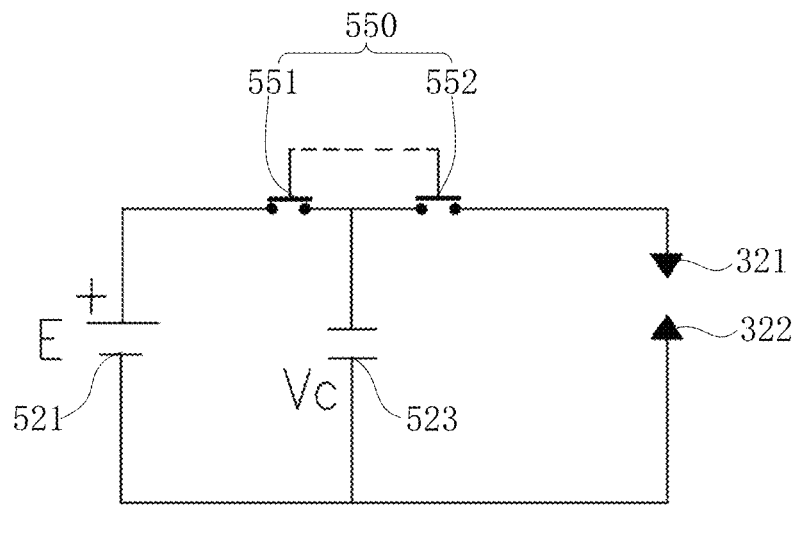
FIG. 4 is a simplified equivalent circuit diagram of a high-voltage generation unit according to the first embodiment of the present invention.
Figure 5:
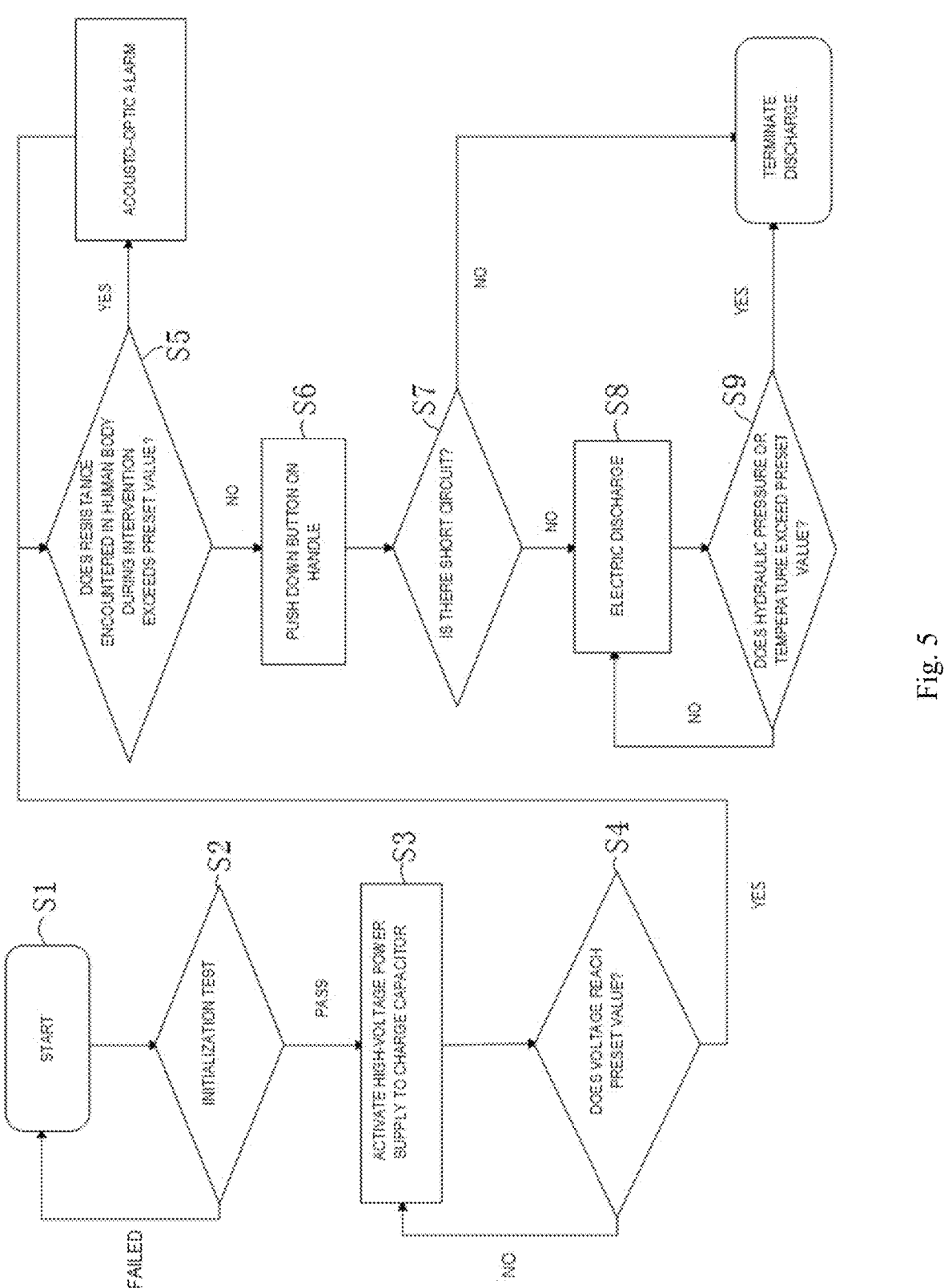
FIG. 5 is a flow diagram of operation of the electrode balloon catheter and the high-voltage generation processing device according to the first embodiment of the present invention.
Figure 6:
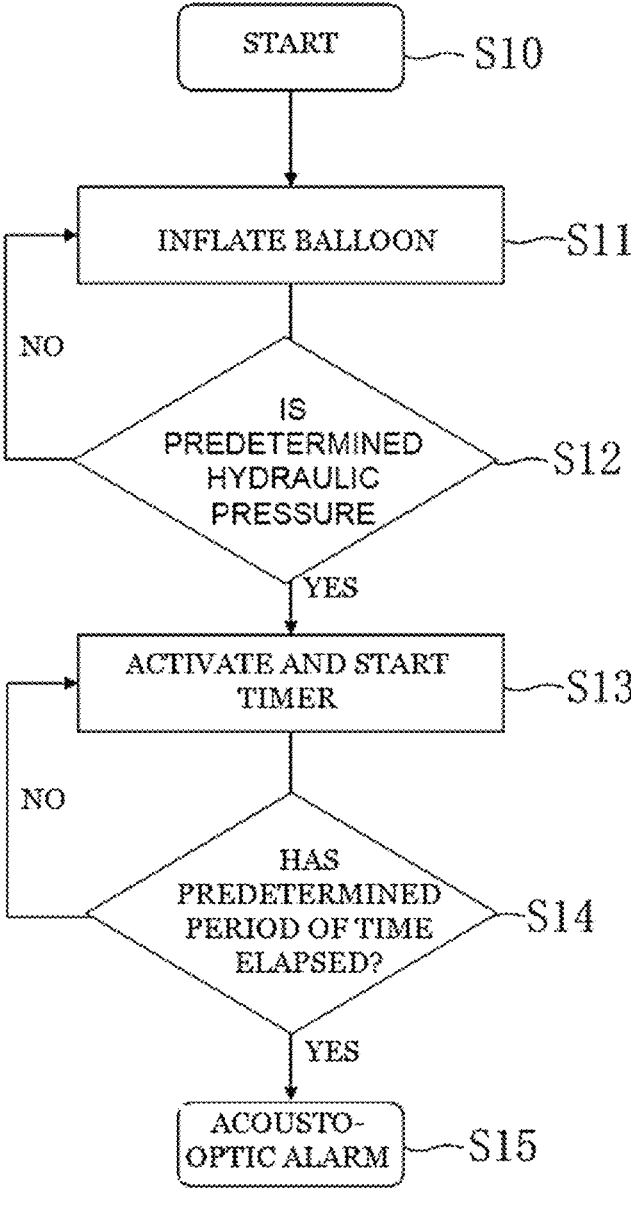
FIG. 6 is a flow diagram of safe operation of the electrode balloon catheter and the high-voltage generation processing device according to the first embodiment of the present invention.
Figure 7A:
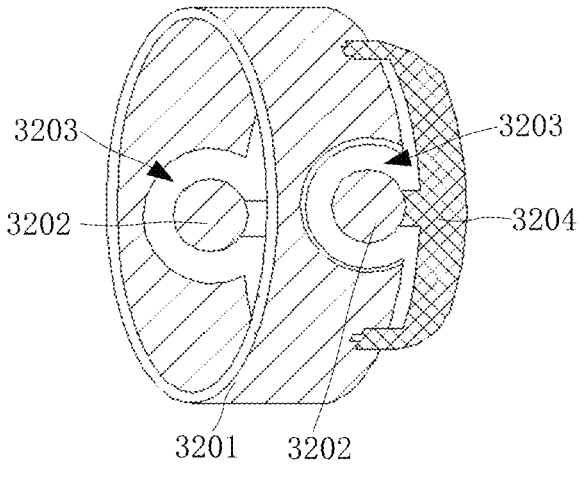
FIG. 7a is a schematic illustration of an electrode arrangement according to the first and third embodiments of the present invention.
Figure 7B:
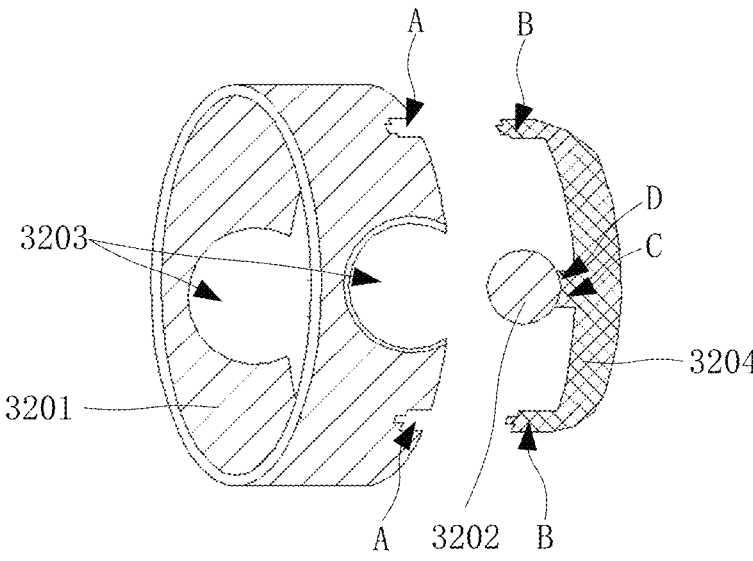
FIG. 7b is another schematic illustration of the electrode arrangement according to the first and third embodiments of the present invention.
Figure 9:
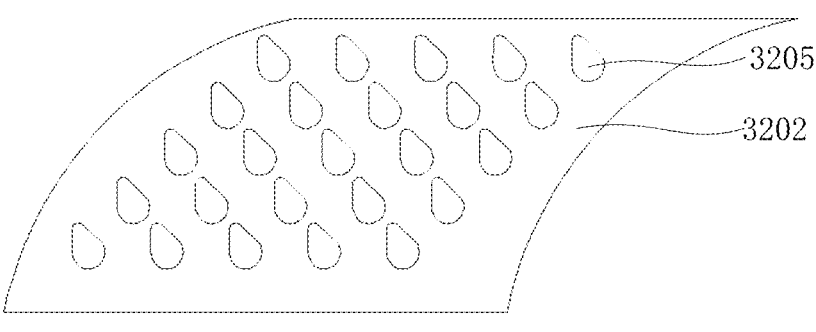
FIG. 9 schematically illustrates pointed protrusions of a first electrode in an electrode arrangement according to the first embodiment of the present invention.

Reference is now made to FIGS. 1 to 7*b*. FIG. 1 is a schematic illustration of an electrode balloon catheter according to a first embodiment of the present invention. FIG. 2 is a schematic illustration of an inner catheter according to the first embodiment of the present invention. FIG. 3 is a circuit diagram of a high-voltage generation processing device according to the first embodiment of the present invention. FIG. 4 is a simplified equivalent circuit diagram of a high-voltage generation unit according to the first embodiment of the present invention. FIG. 5 is a flow diagram of operation of the electrode balloon catheter and the high-voltage generation processing device according to the first embodiment of the present invention. FIG. 6 is a flow diagram of safe operation of the electrode balloon catheter and the high-voltage generation processing device according to the first embodiment of the present invention. FIG. 7*a* is a schematic illustration of an electrode arrangement according to the first and third embodiments of the present invention. FIG. 7*b* is another schematic illustration of the electrode arrangement according to the first and third embodiments of the present invention. FIG. 9 schematically illustrates pointed protrusions of a first electrode in an electrode arrangement according to the first embodiment of the present invention As shown in FIG. 1, the electrode balloon catheter includes a balloon 100, an inner catheter 200 and a shock wave generation component. Preferably, the electrode balloon catheter 100 further includes an outer catheter 400, which is disposed over the inner catheter 200 and joined to the balloon 100.

The balloon 100 is, for example, a shuttle-shaped structure disposed over the inner catheter 200. For example, it may be disposed over a distal end portion of the inner catheter 200. Of course, the balloon 100 may alternatively be a cylindrical structure, and may alternatively be disposed over a portion of the inner catheter 200 between proximal and distal ends thereof. The inner catheter 200 is, for example, a cylinder. The balloon 100 preferably extends along an axial direction of the inner catheter 200. Preferably, a distal end of the balloon 100 is connected to the distal end of the inner catheter 200, and a proximal end of the balloon 100 is joined to a distal end of the outer catheter 400. The balloon 100 can radially expand or collapse under the action of filling and evacuation of an inflation fluid 110. The inflation fluid 110 may be a conductive liquid, which can be filled in or evacuated from the balloon 100, causing expansion or collapse of the balloon 100. An amount of the inflation fluid 110 that can be filled is preferred to be equal to a lumen volume of the balloon 100 in a natural configuration thereof without deformation. The inflation fluid 110 may be a physiological saline solution, a contrast fluid, or a mixture thereof. In other embodiments, the inflation fluid 110 may be a non-conductive liquid, or another inflation fluid suitable for use in human subjects.

The shock wave generation component includes a flexible circuit layer 310 and an electrode arrangement 320.

With combined reference to FIG. 2, the flexible circuit layer 310 is provided on the inner catheter 200. The flexible circuit layer 310 is preferred to have a certain degree of flexibility, a small thickness and other characteristics. The flexible circuit layer 310 is, for example, in the form of a flexible patch attachable to an outer surface of the inner catheter 200. Accordingly, a radial dimension of the electrode balloon catheter may be equal to the sum of a diameter of the inner catheter 200 and a radial dimension of the flexible circuit layer 310. Therefore, compared with conventional balloon catheter designs in which multiple positive and negative electrode leads are bundled together and then attached to an inner catheter, the electrode balloon catheter of this embodiment has a smaller passage size closer to the size of a pre-dilation balloon. Thus, the electrode balloon catheter has improved performance in passage within a human body during intervention without breakage of any component therein. Moreover, the electrode balloon catheter can pass through narrower blood vessel segments and reach a more distal lesion. It would be appreciated that the passage size of the electrode balloon catheter represents a radial dimension of the narrowest blood vessel segment that it can pass through, and the diameter of the pre-dilation balloon refers to a diameter thereof in its non-expanded configuration. Preferably, the flexible circuit layer 310 includes a positive electrode lead 311 and a negative electrode lead 312. More preferably, the flexible circuit layer 310 further includes an insulating protective film. Both the positive electrode lead 311 and the negative electrode lead 312 are provided on the insulating protective film, and the insulating protective film is attached to the inner catheter 200. For example, the positive electrode lead 311 or the negative electrode lead 312 may be implemented as a conductive copper foil. Of course, the positive and negative electrode leads may also be made of other materials with high conductivity, such as gold, silver, platinum and other metal materials. Of course, the flexible circuit layer 310 may also be disposed on an inner surface of the inner catheter 200, or between constituent layers thereof. This can prevent the flexible circuit layer 310 from coming into contact with the inflation fluid 110 on the outer surface of the inner catheter 200, reduce potential hazards. It would be appreciated that a radial dimension of the flexible circuit layer 310 is desired to be as small as possible, as long as it can normally function. This can minimize the passage size of the electrode balloon catheter and make it even closer to a diameter of a pre-dilation balloon. The flexible circuit layer 310 is connected proximally to a high-voltage generation processing device 500 and distally to the electrode arrangement 320. For example, the high-voltage generation processing device 500 includes a high-voltage generation unit 520 capable of delivering high-voltage pulses, which can be relayed by the flexible circuit layer 310 to the electrode arrangement 320 and used thereby to produce shock waves.

With continued reference to FIGS. 1 and 2, the electrode arrangement 320 is provided on the inner catheter 200 and located within the balloon 100 so as to be able to come into contact with the inflation fluid 110 inside the balloon 100. The electrode arrangement 320 is connected to the flexible circuit layer 310 and thereby to the high-voltage generation processing device 500 via the flexible circuit layer 310. Specifically, the electrode arrangement 320 includes a positive electrode 321 and a negative electrode 322. The positive electrode 321 is connected to the positive electrode lead 311, and the negative electrode 322 is connected to the negative electrode lead 312. The shock wave generation component produces shock waves in the manner described below. After the electrode balloon catheter is advanced to a stenotic vessel segment with calcified deposits, the electrode arrangement 320 creates an electrical discharge between the positive and negative electrodes or an arc discharge, which breaks down the inflation fluid 110 in the discharge gap and forms many bubbles therein. Stress from expansion and disappearance of the bubbles will deliver shock waves, which, when propagating to the lesion site, will soften and break up the calcified plaques, thereby destroying the calcified deposits in the blood vessel and re-opening the blood vessel. This therapeutic approach overcomes the shortcomings of conventional balloon angioplasty and has a higher surgical success rate and reduced postoperative complications.

Preferably, the flexible circuit layer 310 has a thickness not exceeding 0.2 mm measured in a radial direction of the inner catheter 200 while allowing the application of a high voltage thereto and flow of a large current therethrough. This enables the electrode balloon catheter to have a passage size close to the size of a pre-dilation balloon. In addition, the flexible circuit layer 310 has excellent bending properties. Further, the radial thickness of the flexible circuit layer 310 may be smaller than 0.1 mm, resulting in an additional reduction in the passage size. Of course, those skilled in the art may configure the thickness of the flexible circuit layer 310 in the radial direction of the inner catheter 200 as actually needed.

Further, in order to achieve better attachment of the flexible circuit layer 310 to the inner catheter 200, the flexible circuit layer 310 is preferably provided on the inner catheter 200 by adhesive bonding, printing, electroplating, 3D printing or vapor deposition. This enables the electrode balloon catheter to have a reduced overall outer diameter and hence improved passage performance. Specifically, the positive and negative electrode leads of the flexible circuit layer 310 may be provided in the same manner as traces in a flexible printed circuit (FPC), and the flexible circuit layer 310 may be adhesively bonded to the inner catheter 200. Alternatively, the positive and negative electrode leads in the flexible circuit layer 310 may be directly printed on the inner catheter 200 in the same manner as traces of a printed circuit. Alternatively, the flexible circuit layer 310 may be provided by electroplating, 3D printing or vapor deposition. Of course, the flexible circuit layer 310 may be provided by a combination of those approaches. For example, the positive electrode lead 311 of the flexible circuit layer 310 may be provided by 3D printing, while the negative electrode lead 312 may be provided by vapor deposition. Alternatively, the positive electrode lead 31 may be provided by electroplating, while the negative electrode lead 312 may be provided by 3D printing. As such, the positive electrode lead 311 and the negative electrode lead 312 may be separately attached to the outer surface of the inner catheter 200. In this way, the positive electrode lead 311 or the negative electrode lead 312 can completely fit on the inner catheter 200, ensuring safety of the circuit. Preferably, the electrode leads of the flexible circuit layer 310 may be connected to the electrode arrangement 320 by laser welding, soldering or crimping. In this first embodiment, the negative electrode lead 312 is connected to the negative electrode 322 by laser welding, and the positive electrode lead 311 is connected to the positive electrode 321 by crimping. Of course, those skilled in the art may determine how the positive electrode lead 311 and the negative electrode lead 312 are connected as actually needed. For example, the positive electrode lead 311 may be connected to the positive electrode 321 by laser welding, while the negative electrode lead 312 may be connected to the negative electrode 322 by crimping.

Further, as shown in FIG. 2, the electrode balloon catheter further includes a temperature sensor 600, which is disposed on the outer surface of the inner catheter 200 or an inner surface of the outer catheter 400 and configured to measure an internal temperature of the balloon 100 and provide a signal indicating the temperature. In this way, during delivery of shock waves, the electrode balloon catheter can monitor the internal temperature of the balloon at any desired time, reducing surgical risk. When electrohydraulic discharge takes place in the inflation fluid, the number of steam bubbles in the inflation fluid will increase, leading to a rise in temperature of the inflation fluid. However, since the temperature of the inflation fluid should not excess a temperature equal to 2° C. plus the normal temperature of the human body, it is necessary to monitor the inflation fluid with the temperature sensor 600 in order to prevent its temperature from rising to an excessive level, which may adversely affect therapeutic efficacy or even harm the health of the health of the human body. During delivery of shock waves, the electrode balloon catheter can monitor the internal temperature of the balloon at any desired time, reducing surgical risk. More preferably, the temperature sensor 600 includes a flexible temperature sensor, which can be attached to the outer surface of the inner catheter 200, allowing the electrode balloon catheter to have a reduced radial dimension. For details of the arrangement of the flexible temperature sensor, reference can be made to the above description in connection with the arrangement of the flexible circuit layer 310, and further description thereof is omitted herein.

Preferably, as shown in FIGS. 1 and 2, the electrode balloon catheter further includes a hydraulic pressure sensor 700, which is provided on the inner catheter 200 and configured to monitor an internal hydraulic pressure of the balloon in real time and provide a signal indicating the inflation pressure. In this way, during delivery of shock waves, the electrode balloon catheter can monitor the internal pressure of the balloon at any desired time, reducing surgical risk. It would be appreciated that there is a clearance between the inner catheter 200 and the outer catheter 400, which is in communication with a lumen of the balloon 100. Therefore, the hydraulic pressure sensor 700 is able to measure the pressure of the inflation fluid in the balloon, regardless of whether it is disposed on the inner catheter 200 or on the outer catheter 400. Preferably, the hydraulic pressure sensor 700 is disposed on the outer surface of the inner catheter 200, or on the inner surface of the outer catheter 400. This can facilitate inflation fluid pressure measurement of the hydraulic pressure sensor 700. More preferably, the hydraulic pressure sensor 700 may be disposed on the inner catheter 200 around the proximal end thereof. In this way, the hydraulic pressure sensor 700 can be provided without leading to an increase in the passage size of the electrode balloon catheter. Preferably, the hydraulic pressure sensor 700 includes a flexible hydraulic pressure sensor, which can be attached to the outer surface of the inner catheter 200m, allowing the electrode balloon catheter to have a reduced radial dimension.

Further, as shown in FIGS. 1 and 2, the electrode balloon catheter further includes a pressure sensor 800, which is disposed at the distal end of the inner catheter 200 and configured to monitor pressure, resistance or pushing force acting on the electrode balloon catheter and provide a resistance signal. In this way, during delivery of shock waves, the electrode balloon catheter can monitor the resistance or pushing force measured by the pressure sensor 800, reducing surgical risk. Preferably, the pressure sensor 800 is in the shape of a ring and disposed over the distal end of the inner catheter 200. This can facilitate comprehensive pressure, resistance or pushing force detection.

Preferably, as shown in FIG. 1, the electrode balloon catheter further includes a catheter connecting member 340 configured for connection with the external high-voltage generation processing device 500 and transmission of high-voltage, detection and other signals therefrom. It would be appreciated that those skilled in the art may configure dimensions of the electrode balloon catheter according to the requirements of the surgical procedure or the patient, such as radial and axial dimensions of the balloon 100 in an inflated configuration thereof, a radial dimension of the inner catheter 200 and the like.

As shown in FIG. 3, in this first embodiment, there is also provided a high-voltage generation processing device 500 configured to be communicatively connected to the electrode balloon catheter. The high-voltage generation processing device 500 includes a logic processing unit 510 and a high-voltage generation unit 520.

As shown in FIG. 3, the logic processing unit 510 is electrically and communicatively connected to the high-voltage generation unit 520 and configured to turn off and on the high-voltage generation unit 520. For example, the logic processing unit 510 may be a logic processor 511 having a logic circuit. The logic processing unit 510 may receive an electrical signal and determine based on the electrical signal whether the high-voltage generation unit 520 is to be turned on or off. The logic processor 511 may be implemented as a STMicroelectronics 32-bit microcontroller (STM32) chip, a field-programmable gate array (FPGA) or the like, in place of a microprocessor.

The logic processing unit 510 is electrically and communicatively connected to the hydraulic pressure sensor 700 in the electrode balloon catheter and configured to receive the inflation pressure signal from the hydraulic pressure sensor 700. When an inflation pressure drop rate or the absolute value of an inflation pressure difference indicated in the inflation pressure signal received at the logic processing unit 510 exceeds a preset threshold, the logic processing unit 510 will cut off electrical and communicative connection within the high-voltage generation unit 520. In other words, the logic processing unit 510 will control the high-voltage generation unit 520 and cause it to cut off a (electrical) connection with an internal circuit of the high-voltage generation unit 520, i.e., cut off a voltage applied across the two electrodes by the high-voltage generation unit 520. When the inflation pressure drop rate or the absolute value of the inflation pressure difference exceeds the preset threshold, it is indicated that the inflation pressure has experienced a steep drop, as detected by the hydraulic pressure sensor 700, possibly as a consequence of bursting of the balloon 100 or another event that may cause such a steep drop in the inflation pressure. The ability of the high-voltage generation unit 520 to cut off the voltage applied across the two electrodes under the control of the logic processing unit 510 ensures safety during operation. Preferably, the high-voltage generation processing device 500 further includes an amplifying circuit 530, which is connected to the logic processing unit 510 at one end and to the hydraulic pressure sensor 700 at the other end. They may be connected communicatively (i.e., electrically) or otherwise to allow the signal to be transmitted from the hydraulic pressure sensor 700 to the logic processing unit 510.

In fact, the shock waves can destroy calcified deposits at a blood vessel lesion and reduce their volumes, thereby widening the vessel's lumen. This can result in a drop in the inflation pressure of the balloon 100 and hence a reduction of its outer diameter, making it unable to completely fit on the blood vessel. Accordingly, the high-voltage generation processing device 500 may further include a display unit 540, which may be, for example, a monitor 541. The display unit 540 may be connected to the logic processing unit 510. When the inflation pressure deviates from a permissible inflation pressure range for normal operation, i.e., when the inflation pressure indicated in the inflation pressure signal exceeds a preset maximum permissible operating pressure value, upon receiving this signal, the logic processing unit 510, which is communicatively connected to the hydraulic pressure sensor 700, may provide the signal to the display unit 540, and the display unit 540 may responsively generate a prompt signal. Preferably, the display unit 540 may have a sound and light generator, and the prompt signal may be provided in the form of an acousto-optic signal. Of course, those skilled in the art may choose other prompt signals in different forms according to the requirements of actual applications.

Preferably, the logic processing unit 510 is also configured to receive the resistance signal from the pressure sensor 800 in the electrode balloon catheter. The pressure sensor 800 can provide protection to the electrode balloon catheter during intervention. When resistance indicated in the resistance signal exceeds a preset threshold, the logic processing unit 510 may pass the resistance signal on to the display unit 540, which may receive the resistance signal and responsively produce an alarm signal. The alarm signal may also be an acousto-optic signal produced by the sound and light generator in the display unit 540. Alternatively, it may be another alarm signal in a different form. It would be appreciated that, according to the law of action-reaction, the resistance can also be considered as a pushing force exerted by the pressure sensor 800. Preferably, one end of the amplifying circuit 530 is connected to the logic processing unit 510, and the other end of the amplifying circuit 530 is connected to the pressure sensor 800, thereby allowing the signal from the pressure sensor 800 to be transmitted to the logic processing unit 510.

More preferably, the logic processing unit 510 is further configured to receive the temperature signal from the temperature sensor 600 in the electrode balloon catheter. In the event of a temperature indicated in the temperature signal exceeds a preset threshold, the logic processing unit 510 may switch off the high-voltage generation unit 520. The ability of the high-voltage generation unit 520 to cut off the voltage applied across the two electrodes under the control of the logic processing unit 510 ensures safety during operation. Preferably, one end of the amplifying circuit 530 is connected to the logic processing unit 510, and the other end of the amplifying circuit 530 is connected to the temperature sensor 600, thereby allowing the signal from the temperature sensor 600 to be transmitted to the logic processing unit 510.

In summary, in the first embodiment, the temperature sensor 600, the hydraulic pressure sensor 700 and the pressure sensor 800 can monitor the internal temperature, pressure and pushing force of the balloon in real time, and the high-voltage generation processing device 500 can take corresponding responsive actions based on the feedback signals therefrom. This improves the efficiency of breaking down calcified lesions, lowers surgical risk and reduces damage to the patient.

Preferably, during delivery of shock waves, in order to avoiding the occurrence of a short-time ventricular capture or shock, the high-voltage generation processing device 500 may monitor in real time a frequency at which shock waves are delivered and a period of time over which the balloon 100 has been inflated. To this end, the high-voltage generation processing device 500 may further include a timer (not shown) connected to the logic processing unit 510. When an inflation pressure indicated in the inflation pressure signal received at the logic processing unit 510 reaches a preset inflation pressure threshold, the timer may be started (it would be appreciated that delivery of shock waves may be started at the same time). For example, after the elapse of a predetermined period of time (e.g., 10 seconds), the timer may issue a timeout signal to the logic processing unit 510, which may then receive the timeout signal and pass it on to the display unit 540. Upon receiving the timeout signal, the display unit 540 may responsively generate a prompt signal prompting the operator to draw the inflation fluid 110 back from the balloon 100. After waiting for a period of time, the operator may again inflate the balloon 100 with the inflation fluid 110 to resume delivery of shock waves. Through providing the timer, the high-voltage generation processing device 500 is able to control time periods for delivery of shock waves, thus additionally reducing surgical risk.

Referring to FIG. 4, the high-voltage generation unit 520 includes a high-voltage generator 521, a high-voltage capacitor 523 and a trigger element 550. The trigger element 550 is connected to the logic processing unit 510. The trigger element 550 is, for example, a trigger device 550a including, for example, a high-voltage relay, an insulated gate bipolar transistor (IGBT) or the like. Of course, those skilled in the art may choose other trigger devices in different forms. The trigger element 550 includes a first switch 551 and a second switch 552. The first switch 551 is disposed between the high-voltage generator 521 and the high-voltage capacitor 523, and second switch 552 is disposed between the high-voltage capacitor 523 and the electrode arrangement 320. The first switch 551 and the second switch 552 can be turned on and off under the control of the logic processing unit 510. When the high-voltage generator 521 is charging the high-voltage capacitor 523, the first switch 551 in the trigger element 550 is closed, while the second switch 552 is open. Upon the electrode balloon catheter reaching a target site, the logic processing unit 510 may control the trigger element 550 to change the states of the first switch 551 and the second switch 552 so that the first switch 551 is open and the second switch 552 is closed. As a result, the high-voltage capacitor 523 applies a voltage across the positive electrode 321 and the negative electrode 322 of the electrode arrangement 320, creating a relatively large current. Moreover, an arc discharge is induced between the positive electrode 321 and negative electrode 322 of the inflation fluid 110, which are soaked in the inflation fluid 110, thus generating shock waves in the inflation fluid 110.

Further, in order to ensure operating safety, as shown in FIG. 3, the high-voltage generation processing device 500 further includes a sampling circuit 560 for detecting a voltage of the high-voltage generation unit 520 and the presence of a short circuit within the electrode arrangement 320 or the flexible circuit layer 310 in the electrode balloon catheter. For example, in order to perform detection on the high-voltage generation unit 520, the operator may detect a voltage of the electrode balloon catheter before the procedure begins. The logic processing unit 510 may issue a signal to the high-voltage generator 521 to cause the latter to generate a high voltage for charging the high-voltage capacitor 523 via a high-voltage resistor 522. Meanwhile, the sampling circuit 560 may sample the voltage and feed it back to the logic processing unit 510, which may then display the sampled voltage on the monitor. For example, in order to perform detection on the electrode arrangement 320 or the flexible circuit layer 310, the high-voltage generator 521 may produce an electrical signal, and the sampling circuit 560 may sample an electrical signal from the electrode arrangement 320 or the flexible circuit layer 310. Only if there is no sign of a short circuit therein, may the operator initiate operation for the minimally-invasive interventional procedure as is conventional.

Preferably, with combined reference to FIGS. 1 and 3, the high-voltage generation processing device 500 further includes a connector 570 and an operating handle 580. As an external connection interface of the high-voltage generation processing device 500, the connector 570 is configured for connection with the electrode balloon catheter. The connector 570 is connected to the catheter connecting member 340 of the electrode balloon catheter so as to allow transmission of high-voltage, detection and other signals from the high-voltage generation processing device 500 to the electrode balloon catheter. Furthermore, the connector 570 is electrically connected to the electrode balloon catheter. The catheter connecting member 340 includes an external positive electrode lead 341 and an external negative electrode lead 342. The external positive electrode lead 341 is connected to the positive electrode lead 311, and the external negative electrode lead 342 is connected to the negative electrode lead 312. The operating handle 580 is used to turn on and off the logic processing unit 510.

Operation of the electrode balloon catheter and the high-voltage generation processing device 500 and wiring of the circuit of the high-voltage generation processing device 500 will be explained below with reference to FIGS. 1 to 6.

First of all, with particular reference to FIG. 3, depending on a target lesion of the patient, such as coronary, perivalvular or valvular, the operator may configure an operating mode of the logic processing unit 510 in the high-voltage generation processing device 500 by setting, for example, a voltage required by the electrode arrangement 320 for delivery of shock waves, an inflation pressure range in an expanded configuration of the balloon 100, a permissible resistance range for the pressure sensor 800 and the like. After mode configuration (i.e., interface selection) is complete, the connector 570 is connected to an electrode balloon catheter with a size compatible with the target lesion. The operator then performs preoperative detection, which involves charging of the high-voltage capacitor 523 via the high-voltage resistor 522 with a high voltage produced by the high-voltage generator 521. Meanwhile, the sampling circuit 560 performs voltage and short circuit detection and feeds the information back to the logic processing unit 510. The information is then displayed on the monitor 541. If it is determined that the voltage is satisfactory and there is no sign of a short circuit, an interventional procedure can be started.

Subsequently, the operator advances the electrode balloon catheter to the blood vessel lesion. During the advancement of the electrode balloon catheter, the pressure sensor 800 feeds pushing force measurements back to the logic processing unit 510 through the amplifying circuit 530. When a pushing force value exceeding a threshold is identified, the monitor 541 will raise an acousto-optic alarm. After reaching the blood vessel lesion, the inflation fluid 110 is filled into the balloon 100, and the hydraulic pressure sensor 700 monitors an internal inflation pressure of the balloon 100 in real time. During delivery of shock waves, the hydraulic pressure sensor 700 and the temperature sensor 600 communicate with the logic processing unit 510 in real time via the amplifying circuit 530 to effect pressure and temperature detection. In the event of an internal temperature value received from the temperature sensor 600 exceeding a warning threshold, the high-voltage generator 521 will cut off the voltage applied between the two electrodes under the control of the logic processing unit 510. If a steep inflation pressure drop being identified from information received from the hydraulic pressure sensor 700, the high-voltage generator 521 will cut off the voltage applied between the two electrodes under the control of the logic processing unit 510. If the inflation pressure of the balloon 100 deviates from a preset permissible inflation pressure range, the monitor 541 will generate a prompt signal. When delivery of shock waves has lasted for a period longer than 10 seconds, the logic processing unit 510 communicates with the monitor 541 and prompts the operator to evacuate the inflation fluid 110 from the balloon 100. After waiting for a period of time, the operator again inflates the balloon 100 with the inflation fluid 310 to resume delivery of shock waves.

Further, with particular reference to FIG. 5, a more detailed process of operation of the electrode balloon catheter and the high-voltage generation processing device 500 according to the first embodiment is described below, which includes the step as follows:

S1: Start.

S2: Perform an initialization test. The high-voltage generation processing device 500 checks whether there are abnormalities in parameters of the electrode balloon catheter and the high-voltage generation processing device 500, such as the presence of a short circuit, an uncontrolled decompression or the like. If all the parameters are within their corresponding bounds, the control proceeds to the next step. If any of the parameters does not stay within the corresponding bounds, the initialization test fails.

S3: Activate the high-voltage power supply to charge the capacitor.

S4: Determine whether a voltage reaches a preset value. Specifically, a voltage across the capacitor may be detected. If the voltage reaches a threshold, the control proceeds to the next step for performing an interventional procedure on the patient's body with the electrode balloon catheter. If not, the previous step is repeated.

S5: Determine whether resistance encountered during the interventional procedure exceeds a preset value. If so, a prompt is provided to the operator in the form of an acousto-optic alarm. If resistance encountered during the interventional procedure does not exceed the preset value and the electrode balloon catheter has successfully reached the target lesion, the balloon 100 is inflated with the inflation fluid 110.

S6: Push down a button on the operating handle 580.

S7: Determine whether there is a short circuit. The high-voltage generation processing device 500 detects whether there is a short circuit in the circuit. Once a short circuit is identified, an electric discharge is terminated. If not so, the control proceeds to the next step.

S8: Induce an electric discharge.

S9: Determine whether a hydraulic pressure or a temperature exceeds a preset value. The hydraulic pressure represents the aforementioned inflation pressure. Steps S9 and S8 may be carried out in parallel. If any of the hydraulic pressure and temperature exceeds the preset value, the electric discharge is terminated. If each of the hydraulic pressure and temperature does not exceed the preset value, the previous step is repeated.

Further, referring to FIG. 6, in order to avoid exposing the patient to a surgical risk such as a short-time ventricular capture or shock, a process for safe operation of the high-voltage generation processing device 500 may be further carried out, which includes the steps as follows:

S10: Issue a signal for inflating the balloon 100 at the beginning of the process.

S11: Inflate the balloon.

S12: Determine whether a predetermined hydraulic pressure is attained. If the internal pressure of the balloon 100 reaches a preset threshold (e.g., 4 atm), the control proceeds to the next step. If not so, the previous step is repeated.

S13: Activate and start the timer.

S14: Determine whether a predetermined period of time has elapsed. If the timer reaches a preset value (e.g., 10 s), the control proceeds to the next step. If not so, the previous step is repeated.

S15: Raise an acousto-optic alarm. Prompted by the acousto-optic alarm, the operator may evacuate the inflation fluid 110 from the balloon 100, improving safety of the surgical procedure.

In the present first embodiment, there is also provided an electrode arrangement 320, as described below in detail with reference to FIGS. 1, 7a and 7b. The electrode arrangement 320 is for use in an electrode balloon catheter. It would be appreciated that the electrode arrangement 320 may be used not only in the electrode balloon catheter as defined above, but also in other electrode balloon catheters such as those with non-flexible positive and negative electrode leads. The electrode arrangement 320 includes a first electrode 3201, a second electrode 3202 and an accommodation structure 3203.

As shown in FIG. 7a, for example, the first electrode 3201 is preferably a ring-shaped structure arranged circumferentially around an electrode balloon catheter, for example, around the inner catheter 200 of the above-discussed electrode balloon catheter. Of course, the first electrode 3201 may also be arranged round other electrode balloon catheters. The first electrode 3201 may alternatively have different shapes. For example, it may be a rectangular sheet, a thin sheet in the form of a patch or the like, etc. It may be provided on the inner catheter 200.

With continued reference to FIG. 7a, the accommodation structure 3203 may be, for example, a circular structure. The accommodation structure 3203 is provided in the first electrode 3201 preferably so as to extend through the first electrode 3201. In other embodiments, the accommodation structure 3203 may be provided in a surface of the first electrode 3201. The accommodation structure 3203 may be provided around either a lateral end or the middle of the first electrode 3201. Of course, the accommodation structure 3203 may alternatively have a rectangular, square, diamond-like, triangular or other shape. Those skilled in the art can configure the shape, size and location of the accommodation structure 3203 according to the position, direction and magnitude of shock waves as required by particular applications. The present embodiment is not limited to any particular shape of the accommodation structure 3203.

With continued reference to FIG. 7a, at least a portion of the second electrode 3202 is disposed in the accommodation structure 3203. Thus, the electrode arrangement 320 is a single-layer arrangement in which the second electrode 3202 and the first electrode 3201 can be considered as different portions of a single layer and an electric discharge can be created therebetween. This arrangement enables the electrode balloon catheter to have a reduced passage size closer to the size of a pre-dilation balloon, and compared to electrode arrangements for creating an electric discharge between laminated electrodes, can avoid the problem of difficult passage of the electrode balloon catheter or even possible breakage of a component therein during intervention. The first electrode 3201 is spaced apart from the second electrode 3202 by a gap to be filled with an inflation fluid. This arrangement enables the electrode balloon catheter to have a reduced passage size as the first electrode 3201 and the second electrode 3202 are parallel and separate while extending within the same plane. For example, the second electrode 3202 is preferably shaped like a sheet. One of the first electrode 3201 and the second electrode 3202 serves as a positive electrode 321, and the other as a negative electrode 322. The first electrode 3201 and the second electrode 3202 are configured for electric connection with a high-voltage generation processing device 500. In the first embodiment, the first electrode 3201 is a positive electrode 321, and the second electrode 3202 is a negative electrode 322. In alternative embodiments, the first electrode 3201 may be a negative electrode 322, whilst the second electrode 3202 may be a positive electrode 321.

Further, as shown in FIG. 7a, at least a portion of the second electrode 3202 has a shape matching that of the accommodation structure 3203. For example, in case of the accommodation structure 3203 being implemented as a circular structure, the at least a portion of second electrode 3202 may also be a circular structure, and in case of the accommodation structure 3203 being implemented as a rectangular structure, the at least a portion of second electrode 3202 may also be a rectangular structure. Of course, alternatively, the second electrode 3202 may be entirely, or at least partially, disposed within the accommodation structure 3203.

Preferably, as shown in FIG. 7a, at least two accommodation structures 3203 may be provided in the first electrode 3201, and one second electrode 3202 may be disposed in each accommodation structure 3203 in the same manner as discussed above. With this arrangement, a single first electrode 3201 can provide at least two shock wave sources, reducing the number of required first electrodes 3201 and achieving increased shock wave generation efficiency.

Preferably, the first electrode 3201 and/or the second electrode 3202 may be provided on an electrode balloon catheter, for example, preferably on the inner catheter 200 of the electrode balloon catheter as detailed above, by adhesive bonding, printing, electroplating, 3D printing or vapor deposition. Of course, it/they may be provided on a carrier of the electrode balloon catheter for carrying the first electrode 3201 and/or the second electrode 3202. For example, the carrier may be the inner catheter 200 or an insulating connecting member 3204. More preferably, the first electrode 3201 and/or the second electrode 3202 may be directly integrally formed with a flexible circuit layer 310. In this embodiment, the second electrode 3202 is directly integrally formed with the flexible circuit layer 310 and thus provides the same benefits as the flexible circuit layer 310, which have been described in detail above and, therefore, needs not be described in further detail herein.

Preferably, the electrode arrangement 320 further includes an insulating connecting member 3204, which is connected to both the first electrode 3201 and the second electrode 3202 and configured to fix the first electrode 3201 and the second electrode 3202 at desired relative positions. In this first embodiment, the insulating connecting member 3204 is configured to fix the second electrode 3202 so that the gap between the second electrode 3202 and the first electrode 3201 is maintained, always enabling the creation of an electric discharge between the first electrode 3201 and the second electrode 3202 in the inflation fluid 110 therebetween. Additionally, as shown in FIG. 7*b*, the second electrode 3202 is fixedly connected to the insulating connecting member 3204, which is snapped onto the first electrode 3201. The insulating connecting member 3204, the first electrode 3201 and the second electrode 3202 are provided on the electrode balloon catheter within the same plane, for example, preferably on the inner catheter 200 of the electrode balloon catheter. Of course, they may also be provided on other electrode balloon catheters in such a manner that the first electrode 3201 and the second electrode 3202 extend within the same plane along an inner catheter 200 while being spaced part from each other. This ensures that the electrode arrangement 320 is a single-layer arrangement which enables the electrode balloon catheter to have a reduced passage size. Specifically, for example, the first electrode 3201 may have a first connecting feature A, which may be a notch, for example. The insulating connecting member 3204 may have a second connecting feature B and a third connecting feature C, which may be both projections, for example. The second electrode 3202 may have a fourth connecting feature D. The second connecting feature B may be snapped into the first connecting feature A, connecting and fixing the insulating connecting member 3204 to the first electrode 3201. The third connecting feature C may be connected to the fourth connecting feature D, connecting and fixing the insulating connecting member 3204 to the second electrode 3202. More specifically, the first electrode 3201 may define two first connecting features A on a single side thereof. The insulating connecting member 3204 may assume a shape resembling the letter "E", which has two lateral projections provided by two second connecting features B and a middle projection provided by one third connecting feature C. Moreover, the second electrode 3202 may define one fourth connecting feature D on a side thereof facing the first electrode 3201. With this arrangement, a gap can be formed between the first electrode 3201 and the second electrode 3202, which ensures that the two will not touch and short to each other. In fact, shock waves created from an electric discharge taking place between the positive and negative electrodes will propagate in a direction perpendicular to the plane of the positive and negative electrodes, i.e., the plane of FIG. 7*a*. According to this embodiment, the electric discharge occurs between the first electrode 3201 and the second electrode 3202 in the same plane as the two electrodes. As a result, the shock waves are delivered in a direction which allows the shock waves to more efficiently reach a target lesion. Preferably, the insulating connecting member 3204 is made of a material with good heat insulation, electric insulation and bending properties. Preferably, the material is polytetrafluoroethylene (PTFE), polyimide (PI) or the like.

As shown in FIG. 9, micron-sized pointed protrusions 3205 arranged into clusters may be provided on surface(s) of the first electrode 3201 and/or the second electrode 3202. The pointed protrusions 3205 have a diameter and a height, which are both micron-sized. Preferably, the height of the pointed protrusions 3205 lies between 1 micron and 100 microns. It would be appreciated that the protrusions may be formed through roughening the surface(s) of the first electrode 3201 and/or the second electrode 3202 by micronscale processing. Preferably, with continued reference to FIG. 9, micron-sized pointed protrusions 3205 are provided on a surface of the negative electrode 322. For example, the pointed protrusions 3205 may extend normally to the electrode's surface. After an electric discharge is induced, under the action of the electrohydraulic effect, shock waves created therefrom will have an increased energy density after passing through the clustered pointed protrusions 3205 formed by micron-scale processing. As a result, the shock waves are more powerful and can destroy a calcified lesion more efficiently. During the electric discharge, an electric spark may be created as a result of electrons moving from the negative electrode to the positive electrode. The surface of the negative electrode is preferably treated by micron-scale processing in order to achieve a significantly increased energy density. In other embodiments, the positive electrode may be likewise treated by micron-scale processing. In this embodiment the second electrode 3202 serves as the negative electrode 322, and its surface is provided with micron-sized pointed protrusions 3205. Of course, the first electrode 3201 and/or the second electrode 3202 may be alternatively treated by nanoscale processing. In this case, utilization of the electrohydraulic effect in the inflation fluid 110 can be achieved in a similar manner as the micron-scale processing case, and further description thereof is omitted herein.

Embodiment 2

Figure 8A:
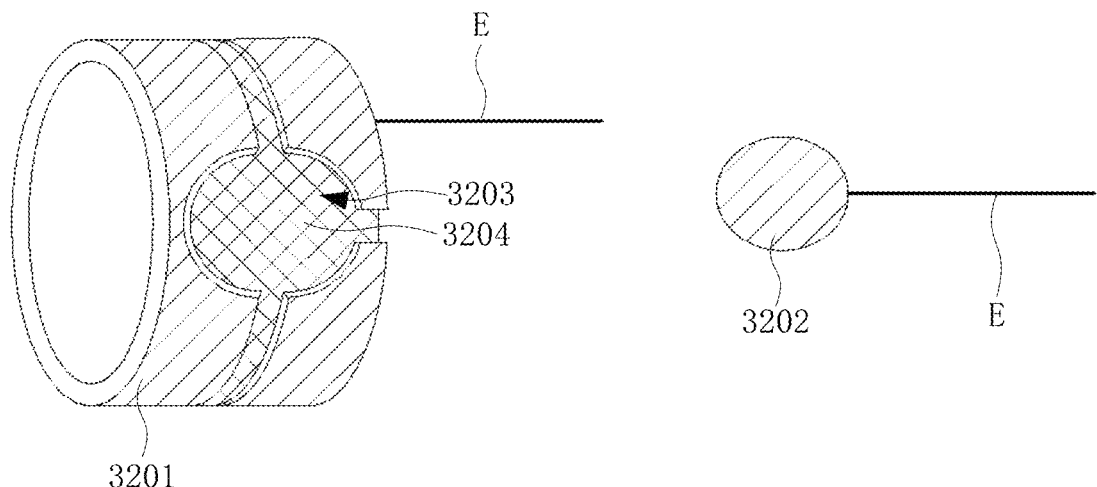
FIG. 8a is a schematic illustration of an electrode arrangement according to second and third embodiments of the present invention.
Figure 8B:
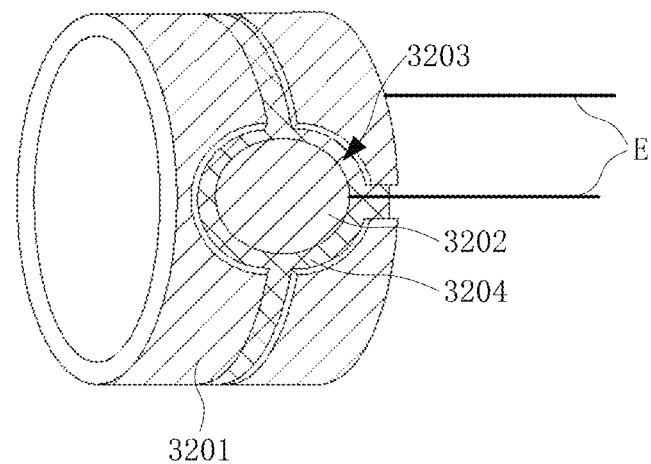
FIG. 8b is another schematic illustration of the electrode arrangement according to the second and third embodiments of the present invention.

Reference is now made to FIG. 8*a*, a schematic illustration of an electrode arrangement according to second and third embodiments of the present invention, and to FIG. 8*b*, another schematic illustration of the electrode arrangement according to the second and third embodiments of the present invention.

In the following, only differences of this second embodiment from the first embodiment will be described, and any feature that it commonly shares with the first embodiment will not be described again.

As shown in FIGS. 8*a* and 8*b*, the insulating connecting member 3204 is arranged in the accommodation structure 3203, and the second electrode 3202 is provided on the insulating connecting member 3204. In this way, the electrode arrangement 320 is also a single-layer arrangement, which, when provided on the inner catheter 200, enables the electrode balloon catheter to have a reduced passage size. Similarly, an electric discharge can be induced between the first electrode 3201 and the second electrode 3202, which occurs in the same plane as the two electrodes. Additionally, the accommodation structure 3203 is directly provided in a surface of the first electrode 3201. In this second embodiment, the accommodation structure 3203 is provided in the form of a depression in the surface of the first electrode 3201. The insulating connecting member 3204 is arranged within the accommodation structure 3203, and the second electrode 3202 is mounted on the insulating connecting member 3204 so as to be also located within the accommodation structure 3203. Similarly, a gap is left between the first electrode 3201 and the second electrode 3202. In an alternative embodiment, the accommodation structure 3203 may extend through the first electrode 3201, which is, for example, attached to the inner catheter 200. In this case, the insulating connecting member 3204 arranged in the accommodation structure 3203 may be directly attached to the inner catheter 200, and the second electrode 3202 may be provided on the insulating connecting member 3204. Of course, both the first electrode 3201 and the second electrode 3202 are directly attached to the inner catheter 200, with the insulating connecting member 3204 spanning the gap therebetween in order to prevent short circuits. The first electrode 3201 and the second electrode 3202 are separately connected to a high-voltage generation processing device by individual electrode leads E. It would be appreciated that the electrode leads E includes a positive electrode lead and a negative electrode lead. The positive electrode is connected to the positive electrode, and the negative electrode is connected to the negative electrode lead.

In this embodiment, the electrode balloon catheter may include one or more electrode arrangements 320 and, in the latter case, each of the electrode arrangements 320 may be implemented either as the electrode arrangement 320 of the first embodiment, or as the electrode arrangement 320 of the second embodiment.

Embodiment 3

FIG. 7a is a schematic illustration of the electrode arrangement according to the first and third embodiments of the present invention. FIG. 7b is another schematic illustration of the electrode arrangement according to the first and third embodiments of the present invention. FIG. 8a is a schematic illustration of the electrode arrangement according to the second and third embodiments of the present invention. FIG. 8b is another schematic illustration of the electrode arrangement according to the second and third embodiments of the present invention.

In the following, only differences of this third embodiment from the first and second embodiments will be described, and any feature that it commonly shares with the first or second embodiment will not be described again.

Referring to FIGS. 7a to 8b, the electrode arrangement 320 in this embodiment is for use in an electrode balloon catheter and includes a first electrode 3201 and a plurality of second electrodes 3202.

The first electrode 3201 defines a plurality of accommodation cavities 3203 each configured to receive therein at least part of a respective one of the plurality of second electrodes 3202. For example, two, three or more second electrodes 3202 and two, three, four or more accommodation cavities 3203 may be included. Preferably, the number of second electrodes 3202 is equal to the number of accommodation cavities 3203. In this way, at least part of each second electrode 3202 can be received in a respective one of the accommodation cavities 3203. Of course, the entirety of each second electrode 3202 may be alternatively received within a respective one of the accommodation cavities 3203. Those skilled in the art may configure the shape, area or the like of the parts of the second electrodes 3202 received in the accommodation cavities 3203 according to the requirements of practical applications.

The first electrode 3201 is spaced apart from the second electrodes 3202 and has a greater area than the second electrodes 3202 so that the second electrodes 3202 can always be received in the first electrode 3201. Reference can be made to the first embodiment for a detailed description of the benefits that the electrode arrangement 320 can provide based on this design, and further description thereof will be omitted here.

One of the first electrode 3201 and the second electrodes 3202 may serve as positive electrode or electrodes, and the other as negative electrode or electrodes. The first electrode 3201 and the second electrode 3202 are configured for electrical connection with a high-voltage generation processing device. Since the first electrode 3201 and the second electrodes 3202 are the same as those of the first embodiment, further description thereof is omitted here.

As shown in FIGS. 7a to 8b, particularly in FIG. 7a, preferably, the first electrode 3201 is a ring-shaped structure disposed over the electrode balloon catheter, and the second electrodes 3202 are circuit discs evenly arranged on a circumference of the first electrode 3201. This enables a uniform distribution of electric discharges created between the positive and negative electrodes and hence uniform expansion of the balloon 100 with respect to the circumference of the first electrode 3201. In this third embodiment, there are two second electrodes 3202, which are evenly arranged on a circumference of the first electrode 3201.

Preferably, as shown in FIGS. 7a and 8b, the first electrode 3201 and the second electrodes 3202 are fixed in position relative to each other by insulating connecting members 3204, which serve not only to provide insulation between the first electrode 3201 and the second electrodes 3202 but also as support means.

Preferably, as shown in FIG. 8a, the insulating connecting members 3204 are disposed within the accommodation cavities 3203, and the second electrodes 3202 are provided on the insulating connecting members 3204, providing for a single-layer arrangement of the second electrodes 3202 and the first electrode 3201.

In summary, the present invention provides an electrode balloon catheter and a high-voltage generation processing device. The electrode balloon catheter includes a balloon, an inner catheter and a shock wave generation component. The balloon is disposed over the inner catheter and radially expands or collapses under the action of filling and evacuation of an inflation fluid therein and therefrom. The shock wave generation component includes a flexible circuit layer and an electrode arrangement. The flexible circuit layer is disposed on the inner catheter, and the electrode arrangement is provided on the inner catheter so as to be located within the balloon. The electrode arrangement is connected to the flexible circuit layer and configured to be connected to a high-voltage generation processing device via the flexible circuit layer. With this arrangement, the flexible circuit layer enables the electrode balloon catheter to have a reduced passage size closer to the size of a pre-dilation balloon, which imparts to the electrode balloon catheter improved performance in passage within a human body during intervention without breakage of any component therein.

The description presented above is merely that of a few preferred embodiments of the present invention and is not intended to limit the scope thereof in any sense. Any and all changes and modifications made by those of ordinary skill in the art based on the above teachings fall within the scope as defined in the appended claims.

What is claimed is:

1. An electrode balloon catheter, comprising a balloon, an inner catheter and a shock wave generation component,
   the balloon disposed over the inner catheter and configured to radially expand or collapse as a result of filling an inflation fluid therein or evacuating the inflation fluid therefrom,
   the shock wave generation component comprising a flexible circuit layer and an electrode arrangement, the electrode arrangement provided on the inner catheter so as to be located within the balloon, the electrode arrangement connected to the flexible circuit layer and configured to be connected to a high-voltage generation processing device via the flexible circuit layer,
   wherein the flexible circuit layer is in the form of a flexible patch, the flexible circuit layer is disposed on an outer surface of the inner catheter, an inner surface of the inner catheter, or between constituent layers of the inner catheter, the electrode arrangement includes a first electrode, a second electrode and an accommodation structure, the first electrode is arranged around the inner catheter, the accommodation structure is provided in the first electrode, at least a portion of the second electrode is disposed in the accommodation structure, thus, the electrode arrangement is a single-layer arrangement.

2. The electrode balloon catheter according to claim 1, wherein the flexible circuit layer has a thickness not exceed 0.2 mm in a radial direction of the inner catheter.

3. The electrode balloon catheter according to claim 2, wherein the flexible circuit layer is provided on the inner catheter by adhesive bonding, printing, electroplating, three-dimensional printing or vapor deposition.

4. The electrode balloon catheter according to claim 1, further comprising a pressure sensor, which is disposed at a distal end of the inner catheter and configured to monitor resistance on the electrode balloon catheter and provide a resistance signal.

5. The electrode balloon catheter according to claim 4, wherein the pressure sensor is ring-shaped and disposed over the distal end of the inner catheter.

6. The electrode balloon catheter according to claim 1, further comprising a hydraulic pressure sensor, which is disposed on the inner catheter and configured to monitor in real time an internal inflation pressure of the balloon and provide an inflation pressure signal.

7. The electrode balloon catheter according to claim 6, further comprising an outer catheter disposed over the inner catheter so as to communicate with the balloon, wherein the hydraulic pressure sensor is provided on the outer surface of the inner catheter or an inner surface of the outer catheter.

8. The electrode balloon catheter according to claim 6, further comprising a temperature sensor, which is disposed on the outer surface of the inner catheter or an inner surface of the outer catheter and configured to monitor an internal temperature of the balloon in real time and provide a temperature signal.

9. A high-voltage generation processing device, configured for communicative connection with the electrode balloon catheter according to claim 1, the high-voltage generation processing device comprising a logic processing unit and a high-voltage generation unit, the logic processing unit electrically and communicatively connected to the high-voltage generation unit and configured to turn on and off the high-voltage generation unit, the logic processing unit electrically and communicatively connected to an hydraulic pressure sensor in the electrode balloon catheter and configured to receive an inflation pressure signal from the hydraulic pressure sensor and, when an inflation pressure drop rate or an absolute value of an inflation pressure difference indicated in the inflation pressure signal received by the logic processing unit exceeds a preset threshold, cut off the electrical and communicative connection with the high-voltage generation unit.

10. The high-voltage generation processing device according to claim 9, further comprising a display unit connected to the logic processing unit, wherein when an inflation pressure indicated in the inflation pressure signal exceeds a preset operating pressure, the logic processing unit passes the inflation pressure signal on to the display unit which then provides a prompt signal upon receiving the inflation pressure signal.

11. The high-voltage generation processing device according to claim 9, wherein the logic processing unit is further configured to receive a resistance signal from the pressure sensor in the electrode balloon catheter, and when resistance indicated in the resistance signal exceeds a preset threshold, pass the resistance signal on to the display unit which then provides an alarm signal upon receiving the resistance signal.

12. The high-voltage generation processing device according to claim 9, wherein the logic processing unit is further configured to receive a temperature signal from a temperature sensor in the electrode balloon catheter, and when a temperature indicated in the temperature signal exceeds a preset threshold, cut off the high-voltage generation unit.

13. The high-voltage generation processing device according to claim 9, further comprising an amplifying circuit, one end of the amplifying circuit connected to the logic processing unit, a further end of the amplifying circuit connected to the hydraulic pressure sensor, a touch sensor or a temperature sensor in the electrode balloon catheter.

14. The high-voltage generation processing device according to claim 9, further comprising a timer, which is connected to the logic processing unit and configured to be started when an inflation pressure indicated in the inflation pressure signal received by the logic processing unit reaches a preset inflation pressure and send a timeout signal to the logic processing unit after a predetermined period of time elapses, wherein upon receiving the timeout signal, the logic processing unit passes the timeout signal on to the display unit which then provides a prompt signal upon receiving the timeout signal.

15. The high-voltage generation processing device according to claim 9, further comprising a sampling circuit for detecting a voltage signal of the high-voltage generation unit and the presence of a short circuit in the electrode arrangement or the flexible circuit layer in the electrode balloon catheter.

* * * * *